United States Patent
Fukui et al.

(10) Patent No.: US 10,512,263 B2
(45) Date of Patent: *Dec. 24, 2019

(54) AQUEOUS SUSPENSION AGROCHEMICAL COMPOSITION

(71) Applicant: Sumitomo Chemical Company, Limited, Tokyo (JP)

(72) Inventors: Yusuke Fukui, Takarazuka (JP); Naoki Tsuda, Tokyo (JP); Maki Owaki, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/679,492

(22) Filed: Aug. 17, 2017

(65) Prior Publication Data

US 2017/0339948 A1 Nov. 30, 2017

Related U.S. Application Data

(62) Division of application No. 14/770,515, filed as application No. PCT/JP2014/055205 on Feb. 25, 2014.

(30) Foreign Application Priority Data

Feb. 28, 2013 (JP) ................................ 2013-038434

(51) Int. Cl.
    *A01N 25/04* (2006.01)
    *A01N 43/38* (2006.01)
    *A01N 43/56* (2006.01)

(52) U.S. Cl.
    CPC ............. *A01N 25/04* (2013.01); *A01N 43/38* (2013.01); *A01N 43/56* (2013.01)

(58) Field of Classification Search
None
See application file for complete search history.

(56) References Cited

U.S. PATENT DOCUMENTS

| | | | |
|---|---|---|---|
| 5,723,141 | A | 3/1998 | Kimura et al. |
| 6,521,568 | B1 | 2/2003 | Kimura |
| 9,596,844 | B2 | 3/2017 | Yanagisawa |
| 2012/0035054 | A1 | 2/2012 | Ehr et al. |
| 2015/0173351 | A1 | 6/2015 | Yanagisawa et al. |
| 2015/0366209 | A1 | 12/2015 | Yanagisawa et al. |

FOREIGN PATENT DOCUMENTS

| | | |
|---|---|---|
| CN | 103858904 A | 6/2014 |
| EP | 1222856 A1 | 7/2002 |
| JP | H05105606 A | 4/1993 |
| JP | 2010189354 A | 9/2010 |
| WO | 2012005371 A1 | 1/2012 |
| WO | 2012121413 A1 | 9/2012 |
| WO | 2014003082 A1 | 1/2014 |
| WO | 2014003084 A1 | 1/2014 |

OTHER PUBLICATIONS

Beer, "Valent seeks US fenpyrazamine approval," pp. 1 (2011).
Cabras et al., "Pesticide Residues in Garpes, Wine, and Their Processing Products," Journal of Agricultural and Food Chemistry, vol. 48, No. 4 (2000).
Office Action dated Apr. 28, 2016 in CN Application No. 201480010203.7.
Supplemental Search Report dated Jul. 21, 2016 in EP Application No. 14757241.
Search Opinion dated Jul. 21, 2016 in EP Application No. 14757241.6.
Dombrowski et al., "Dispersion and Grinding of Pesticides," Advances in Pesticide Formulation Technology, Scher, vol. 254, pp. 63-73 (1984).
Office Action dated Jul. 30, 2018 in U.S. Appl. No. 14/770,515, by Fukui.
Office Action dated Nov. 16, 2018 in EP Application No. 14757241.6.
Office Action dated May 19, 2019 in BR Application No. 112015020076-1.
Office Action dated Jul. 31, 2019 in BR Application No. 112015020076-1.
Anonymous, "Conclusion on the peer review of the pesticide risk assessment of the active substance fenpyrazamine: Peer Review of the pesticide risk assessment of the active substance fenpyrazamine," The EFSA Journal, vol. 10, No. 1, 62 pages ((2012).
Office Action dated Jan. 29, 2018 in U.S. Appl. No. 14/770,515, by Fukui.
Office Action dated Apr. 3, 2018 in EP Application No. 14 757 241.6.
Office Action dated Sep. 20, 2019 in KR Application No. 1020157025479.

*Primary Examiner* — Hasan S Ahmed
*Assistant Examiner* — Frank Choi
(74) *Attorney, Agent, or Firm* — Panitch Schwarze Belisario & Nadel LLP

(57) ABSTRACT

An aqueous suspension agrochemical composition is provided containing fenpyrazamine and an acid component. The composition has no problem of emission of odor and has excellent storage stability. The composition has a pH at 25° C. in a range of 2.5 to 6.5.

9 Claims, No Drawings

AQUEOUS SUSPENSION AGROCHEMICAL COMPOSITION

CROSS-REFERENCE TO RELATED APPLICATION

This application is a Divisional of co-pending U.S. patent application Ser. No. 14/770,515, filed Aug. 26, 2015, which is a Section 371 of International Application No. PCT/JP2014/055205, filed Feb. 25, 2014, which was published in the Japanese language on Sep. 4, 2014, under International Publication No. WO 2014/133181 A1, and the disclosures of which are incorporated herein by reference.

TECHNICAL FIELD

The present invention relates to an aqueous suspension agrochemical composition comprising fenpyrazamine.

BACKGROUND ART

Conventionally, an agrochemical formulation comprising fenpyrazamine has been known as an agricultural fungicide, and for example, a granular agrochemical composition and aqueous suspension agrochemical composition comprising fenpyrazamine and lignin sulfonate are practically used (for example, see JP-A-2006-249067 and JP-A-2010-189354).

The formulation sometimes may emit an odor, for example, during storage or transportation under a high temperature, and the like. In most cases in which odor is emitted, they do not involve quality degradation causing a practical problem such as decomposition of agrochemical active ingredient. However, the odor may be recognized as an unpleasant odor, depending on the user and the use situation, thus it is desired to suppress the emission of odor.

An object of the present invention is to provide a fenpyrazamine-containing aqueous suspension agrochemical composition which has no problem of emission of odor and also has excellent storage stability.

DISCLOSURE OF THE INVENTION

The present inventors and the like have studied to find a fenpyrazamine-containing aqueous suspension agrochemical composition which has no problem of emission of odor and also has excellent storage stability, and consequently achieved the present invention.

More specifically, the present invention is as described below.

[1] An aqueous suspension agrochemical composition comprising fenpyrazamine and an acid component, wherein the composition has a pH at 25° C. in the range of 2.5 to 6.5.
[2] The aqueous suspension agrochemical composition according to [1], wherein the acid component is at least one selected from the group consisting of phosphoric acid, hydrochloric acid, and sulfuric acid.
[3] The aqueous suspension agrochemical composition according to [1] or [2], further comprising procymidone.
[4] The aqueous suspension agrochemical composition according to [3], further comprising polyoxyalkylene aryl phenyl ether phosphoric acid ester salt.

According to the present invention, a fenpyrazamine-containing aqueous suspension agrochemical composition which has no problem of emission of odor and also has excellent storage stability can be provided.

MODE FOR CARRYING OUT THE INVENTION

The aqueous suspension agrochemical composition of the present invention (hereinafter, referred to as the present composition) comprises fenpyrazamine, in an amount of usually 1 to 50% by weight, based on 100% by weight of the present composition.

The present composition has a pH at 25° C. in the range of 2.5 to 6.5.

In the present composition, the pH at 25° C. is a pH value that is measured while a glass electrode of a glass electrode type hydrogen ion densitometer (model: D-51, manufactured by HORIBA, Ltd.) is immersed in a stock solution of the present composition that is maintained at 25° C. using a thermostat bath or the like, the pH value determined at a point where the change of the potential difference in 10 seconds is stabilized to within ±1 mV.

As a means for obtaining the present composition having a pH at 25° C. in the range of 2.5 to 6.5, an acid component in an amount required for having the pH in the range of 2.5 to 6.5 is added. The acid component includes inorganic acids, organic acids, and the like. The inorganic acids include hydrochloric acid, hypochlorous acid, sulfuric acid, sulfurous acid, nitric acid, phosphoric acid, boric acid, and the like. The organic acids include saturated or unsaturated fatty acids such as acetic acid, propionic acid, butyric acid, octanoic acid, palmitic acid, oleic acid, stearic acid and HARTALL fatty acid (extract from timber composed mainly of oleic acid and linoleic acid, and also referred to as tall oil fatty acid: manufactured by Harima Chemicals Group, Inc.), aromatic carboxylic acids such as benzoic acid and phthalic acid, di- or tri-carboxylic acids such as succinic acid, malic acid, oxalic acid and citric acid, carboxylic acids such as sorbic acid and lactic acid, organic phosphoric acids such as C1 to C6 mono- or di-alkyl phosphates (for example, diisopropylphosphate, monoisopropylphosphate, PAP (mixture composed mainly of diisopropylphosphate and monoisopropylphosphate: manufactured by NIPPON CHEMICAL INDUSTRIAL CO., LTD.)), and the like. Phosphoric acid, hydrochloric acid or sulfuric acid is preferably used.

The present composition comprises the acid component in an amount of usually 0 to 3.0% by weight, preferably 0.01 to 2.0% by weight, and more preferably 0.01 to 1.0% by weight, as a total amount, based on 100% by weight of the present composition.

The water used in the present composition is not particularly limited, and water used in the normal aqueous suspension agrochemical composition such as tap water, well water and deionized water can be used. Deionized water is preferably used.

The present composition comprises water, in an amount of usually 30 to 80% by weight, based on 100% by weight of the present composition.

The present composition may further comprise an agrochemical adjuvant used in the normal aqueous suspension agrochemical composition. The agrochemical adjuvant includes surfactants, thickeners, antifoaming agents, preservatives, antifreezing agents, and the like.

The surfactants include nonionic surfactants, cationic surfactants, anionic surfactants, and ampholytic surfactants. Examples of the nonionic surfactant include polyoxyethylene alkyl ether, polyoxyethylene alkyl aryl ether, polyoxyethylene lanolin alcohol, polyoxyethylene alkylphenol formalin condensate, polyoxyethylene sorbitan fatty acid ester, polyoxyethylene glyceryl monofatty acid ester, polyoxypropylene glycol monofatty acid ester, polyoxyethylene sorbitol fatty acid ester, polyoxyethylene castor oil derivative, polyoxyethylene fatty acid ester, higher fatty acid glycerol ester, sorbitan fatty acid ester, sucrose fatty acid ester, polyoxyethylene polyoxypropylene block polymer, polyoxyethylene fatty acid amide, alkylol amide, polyoxyethylene alkylamine, and polyoxyethylene alkanediol.

Examples of the cationic surfactant include alkylamine hydrochlorides such as dodecylamine hydrochloride; alkyl quaternary ammonium salts such as dodecyltrimethyl ammonium salt, alkyldimethylbenzyl ammonium salt, alkylpyridinium salt, alkylisoquinolinium salt and dialkylmorpholinium salt; benzethonium chloride, and polyalkyl vinyl pyridinium salt.

Examples of the anionic surfactant include fatty acid sodium such as sodium palmitate; sodium ether carboxylate such as sodium polyoxyethylene lauryl ether carboxylate; amino acid condensates of higher fatty acid, such as sodium lauroyl sarcosine and sodium N-lauroyl glutamate; higher fatty acid ester sulfonates such as higher alkyl sulfonate and lauric acid ester sulfonic acid salt; dialkyl sulfosuccinates such as dioctyl sulfosuccinate; higher fatty acid amide sulfonates such as oleic acid amide sulfonic acid; alkyl aryl sulfonates such as sodium dodecylbenzene sulfonate and diisopropyl naphthalene sulfonate; higher alcohol sulfuric acid ester salts such as formalin condensate of alkyl aryl sulfonate and pentadecane-2-sulfate; polyoxyethylene alkyl phosphoric acid ester salt such as dipolyoxyethylene dodecyl ether phosphate ester; styrene-maleic acid copolymer; lignin sulfonate; and polyoxyalkylene aryl phenyl ether phosphoric acid ester salt.

Examples of the ampholytic surfactant include N-laurylalanine, N,N,N-trimethylaminopropionic acid, N,N,N-trihydroxyethylaminopropionic acid, N-hexyl-N,N-dimethylaminoacetic acid, 1-(2-carboxyethyl)pyridinium betaine, and lecithin.

Among the above surfactants, lignin sulfonate is preferably used. Examples of the lignin sulfonate used in the present invention include sodium salts, potassium salts and ammonium salts of lignin sulfonic acid. As the lignin sulfonate, those having a weight average molecular weight of 4000 or more and preferably about 4000 to 11000, and a sulfonation degree of 1.9 or less and preferably about 0.5 to 1.9 are used. The sulfonation degree of the lignin sulfonate refers to the average number of sulfonic acid groups in one unit, when the molecular weight of one unit of lignin is 1000.

When the present composition comprises a surfactant, the total content thereof is usually 0.1 to 10% by weight, based on 100% by weight of the present composition.

Examples of the thickener include natural polysaccharides such as xanthan gum, rhamsan gum, locust bean gum, guar gum, carrageenan, welan gum, alginic acid, alginate and tragacanth gum; mineral powders such as aluminum silicate, magnesium aluminum silicate, smectite, bentonite, hectorite, synthetic hydrous silicic acid and dry silica; and alumina sol. It is possible to use, as these thickeners, commercially available products as they are. Examples of commercially available products include KELZAN S (trade name of CP Kelco) as xanthan gum, VEEGUM R (trade name of R.T. Vanderbilt Company, Inc.) as aluminum silicate, and Aerosil 200 (trade name of NIPPON AEROSIL CO., LTD.) as dry silica.

When the present composition comprises a thickener, the total content thereof is usually 0.1 to 5% by weight, based on 100% by weight of the present composition.

Examples of the antifoaming agent include silicone-based antifoaming agents such as ANTIFOAM C EMULSION (trade name of Dow Corning Toray Co., Ltd.), ANTIFOAM CE (trade name of Dow Corning Toray Co., Ltd.), ANTIFOAM A COMPOUND (trade name of Dow Corning Toray Co., Ltd.), FS ANTIFOAM 1266 (trade name of Dow Corning Toray Co., Ltd.), KM-98 (trade name of Shin-Etsu Chemical Co., Ltd.), KS-530 (trade name of Shin-Etsu Chemical Co., Ltd.), KS-538 (trade name of Shin-Etsu Chemical Co., Ltd.), BREAK-THRU AF5503 (trade name of Evonik Industries AG), ANTIFOAM E-20 (trade name of Kao Corporation), TSA730 (trade name of Momentive Performance Materials Inc.), TSA731 (trade name of Momentive Performance Materials Inc.), TSA732 (trade name of Momentive Performance Materials Inc.) and YMA6509 (trade name of Momentive Performance Materials Inc.); and fluorine antifoaming agents such as FLUOWET PL80 (trade name of Clariant); FoamStar W220 (trade name of Cognis Japan Ltd.).

When the present composition comprises an antifoaming agent, the total content thereof is usually 0.05 to 0.5% by weight, based on 100% by weight of the present composition.

Examples of the preservative include p-hydroxybenzoic acid esters, salicylic acid derivatives, 1,2-benzisothiazolin-3-one (for example, Proxel GXL (trade name of Lonza Group Ltd.)) and isothiazolin-3-one derivatives (for example, bio-hope L (trade name of KI Chemical Industry Co., Ltd.)).

When the present composition comprises a preservative, the total content thereof is usually 0.01 to 3% by weight, based on 100% by weight of the present composition.

Examples of the antifreezing agent include water-soluble glycols such as ethylene glycol and propylene glycol.

When the present composition comprises an antifreezing agent, the total content thereof is usually 1 to 20% by weight, based on 100% by weight of the present composition.

The present composition may further comprise an agrochemical active ingredient other than fenpyrazamine. The agrochemical active ingredient includes insecticidal active ingredients, fungicidal active ingredients, herbicidal active ingredients, plant growth regulating active ingredients, and the like.

Examples of the insecticidal active ingredient include pyrethroid compounds such as cyfluthrin, cypermethrin, deltamethrin, fenpropathrin, esfenvalerate, tralomethrin, acrinathrin, bifenthrin, resmethrin and tetramethrin; carbamate compounds such as propoxur, isoprocarb, xylylcarb, metolcarb, XMC, carbaryl, pirimicarb, carbofuran, methomyl, oxamyl, fenoxycarb, alanycarb, metoxadiazone, benfuracarb, carbosulfan, furathiocarb, PHC and bendiocarb; organophosphorus compounds such as acephate, phenthoate, vamidothion, trichlorfon, monocrotophos, tetrachlorvinphos, dimethylvinphos, phosalone, chlorpyrifos, chlorpyrifos-methyl, pyridafenthion, quinalphos, methidathion, methamidophos, dimethoate, ethylthiometon, propaphos, formothion, azinphos-ethyl, azinphos-methyl and salithion; urea compounds having a chitin synthesis inhibitory activity such as diflubenzuron, chlorfluazuron, lufenuron, hexaflumuron, flufenoxuron, flucycloxuron, cyromazine, diafenthiuron, hexythiazox, novaluron, teflubenzuron, triflumuron, 4-chloro-2-(2-chloro-2-methylpropyl)-5-(6-iodo-3-pyridylmethoxy)pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2H-1,3,5-thiadiazon-4-one and 1-(2,6-difluorobenzoyl)-3-[2-fluoro-4-(1,1,2,2-tetrafluoroethoxy)phenyl]urea; pyrazole compounds such as 5-amino-4-dichlorofluoromethylsulfenyl-1-(2,6-dichloro-4-trifluoromethylphenyl) pyrazole and 5-amino-1-(2,6-dichloro-4-trifluoromethylphenyl)-4-trifluoromethylsulfenylpyrazole; chloronicotinyl compounds such as imidacloprid, acetamiprid, nitenpyram, diacloden, clothianidin, thiamethoxam, dinotefuran and thiacloprid; macrolide compounds such as spinosad; cartap hydrochloride, buprofezin, thiocyclam, fenoxycarb, fenazaquin, fenpyroximate, pyridaben, pyriproxyfen, fipronil, ethiprole, acetoprole, diazinon hydramethylnon, thiodicarb, chlorfenapyr, fenpyroximate, pymetrozine, pyrimidifen, tebufenozide, tebufenpyrad, triazamate, indoxacarb, sulfluramide, milbemectin, avermectin, clofentezine, boric acid, and paradichlorobenzene.

Examples of the fungicidal active ingredient include benzimidazole compounds such as benomyl, carbendazim, thiabendazole and thiophanate-methyl; phenylcarbamate compounds such as diethofencarb; dithiocarbamate compounds such as thiuram; dicarboximide compounds such as procymidone, iprodione and vinclozolin; azole compounds such as diniconazole, epoxiconazole, tebuconazole, difenoconazole, cyproconazole, flusilazole, triadimefon and hexaconazole; acylalanine compounds such as metalaxyl; carboxyamide compounds such as furametpyr, mepronil, tiadinil, flutolanil and thifluzamide; organophosphorus compounds such as tolclofos-methyl, fosetyl-aluminium and pyrazophos; cyanopyrrole compounds such as fludioxonil and fenpiclonil; antibiotics such as Blasticidin S, kasugamycin, polyoxin, validamycin and mildiomycin; methoxyacrylate compounds such as kresoxim-methyl and metominostrobin; oxadixyl, PCNB, hydroxyisoxazole, dazomet, diclomezine, triazine, isoprothiolane, diclocymet, orysastrobin, carpropamid, chlorothalonil, manzeb, captan, folpet, oxine-copper, basic copper chloride, tricyclazole, pyroquilon, probenazole, fthalide, Acibenzolar S-methyl, cymoxanil, dimethomorph, S-methylbenzo[1.2.3]thiadiazole-7-carbothioate, famoxadone, oxolinic acid, fluazinam, chlobenthiazone, isovaledione, simeconazole, tetrachloroisophthalonitrile, thiophthalimide oxybisphenoxarsine, 3-iodo-2-propylbutyl carbamate, silver zeolite, silver-silica gel, silver zirconium phosphate, parahydroxybenzoic acid esters, sodium dehydroacetate, and potassium sorbate.

Examples of the herbicidal active ingredient include triazine compounds such as atrazine and metribuzin; urea compounds such as fluometuron, isoproturon and dymron; hydroxybenzonitrile compounds such as bromoxynil and ioxynil; 2,6-dinitroaniline compounds such as pendimethalin and trifluralin; aryloxyalkanoic acid compounds such as 2,4-D, dicamba, fluroxypyr and mecoprop; sulfonylurea compounds such as bensulfuron-methyl, metsulfuron-methyl, nicosulfuron, primisulfuron-methyl, cyclosulfamuron, imazosulfuron and 1-(2-chloro-6-propylimidazo[1,2-b]pyridazine-3-ylsulfonyl)-3-(4,6-dimethoxy-pyrimidin-2-yl)urea; imidazolinone compounds such as imazapyr, imazaquin and imazethapyr; bispyribac-sodium, bisthiobac-sodium, acifluorfen-sodium, sulfentrazone, paraquat, flumetsulam, triflusulfuron-methyl, fenoxaprop-p-ethyl, cyhalofop-butyl, diflufenican, norflurazon, isoxachlortole, bentazon, benthiocarb, mefenacet, propanyl, flutiamide, simetryn, fentrazamide, etobenzanid, swep, oxaziclomefone, oxadiazolone, pyrazolate, prodiamine, cafenstrole, pentoxazone, clomeprop, pyriftalid, benzobicyclon, bromobutide, and pyraclonil.

Examples of the plant growth regulating active ingredient include maleic hydrazide, chlormequat, ethephon, gibberellin, mepiquat chloride, thidiazuron, inabenfide, paclobutrazol, and uniconazole.

When the present composition comprises an agrochemical active ingredient other than fenpyrazamine, the total content thereof is usually 1 to 50% by weight, based on 100% by weight of the present composition.

Next, some examples of the present composition are shown below. Here, the amount shows a weight based on the total weight of the present composition.

An aqueous suspension agrochemical composition comprising 1 to 50% by weight of fenpyrazamine and 0 to 3.0% by weight of an acid component, and having a pH at 25° C. of 2.5 or more and 6.5 or less.

An aqueous suspension agrochemical composition comprising 1 to 50% by weight of fenpyrazamine and 0.01 to 2.0% by weight of an acid component, and having a pH at 25° C. of 2.5 or more and 6.5 or less.

An aqueous suspension agrochemical composition comprising 1 to 50% by weight of fenpyrazamine and 0.01 to 1.0% by weight of an acid component, and having a pH at 25° C. of 2.5 or more and 6.5 or less.

An aqueous suspension agrochemical composition comprising 1 to 50% by weight of fenpyrazamine and 0 to 3.0% by weight of one or more acid components selected from phosphoric acid, hydrochloric acid and sulfuric acid, and having a pH at 25° C. of 2.5 or more and 6.5 or less.

An aqueous suspension agrochemical composition comprising 1 to 50% by weight of fenpyrazamine and 0.01 to 2.0% by weight of one or more acid components selected from phosphoric acid, hydrochloric acid and sulfuric acid, and having a pH at 25° C. of 2.5 or more and 6.5 or less.

An aqueous suspension agrochemical composition comprising 1 to 50% by weight of fenpyrazamine and 0.01 to 1.0% by weight of one or more acid components selected from phosphoric acid, hydrochloric acid and sulfuric acid, and having a pH at 25° C. of 2.5 or more and 6.5 or less.

An aqueous suspension agrochemical composition comprising 1 to 50% by weight of fenpyrazamine and 0 to 3.0% by weight of an acid component, and having a pH at 25° C. of 3.0 or more and 6.5 or less.

An aqueous suspension agrochemical composition comprising 1 to 50% by weight of fenpyrazamine and 0.01 to 2.0% by weight of an acid component, and having a pH at 25° C. of 3.0 or more and 6.5 or less.

An aqueous suspension agrochemical composition comprising 1 to 50% by weight of fenpyrazamine and 0.01 to 1.0% by weight of an acid component, and having a pH at 25° C. of 3.0 or more and 6.5 or less.

An aqueous suspension agrochemical composition comprising 1 to 50% by weight of fenpyrazamine and 0 to 3.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine and 0.01 to 2.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine and 0.01 to 1.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine, 1 to 50% by weight of procymidone and 0 to 3.0% by weight of an acid component, and having a pH at 25° C. of 2.5 or more and 6.5 or less.

An aqueous suspension agrochemical composition comprising 1 to 50% by weight of fenpyrazamine, 1 to 50% by weight of procymidone and 0.01 to 2.0% by weight of an acid component, and having a pH at 25° C. of 2.5 or more and 6.5 or less.

An aqueous suspension agrochemical composition comprising 1 to 50% by weight of fenpyrazamine, 1 to 50% by weight of procymidone and 0.01 to 1.0% by weight of an acid component, and having a pH at 25° C. of 2.5 or more and 6.5 or less.

An aqueous suspension agrochemical composition comprising 1 to 50% by weight of fenpyrazamine, 1 to 50% by weight of procymidone, and 0 to 3.0% by weight of one or more acid components selected from phosphoric acid, hydrochloric acid and sulfuric acid, and having a pH at 25° C. of 2.5 or more and 6.5 or less.

An aqueous suspension agrochemical composition comprising 1 to 50% by weight of fenpyrazamine, 1 to 50% by weight of procymidone, and 0.01 to 2.0% by weight of one or more acid components selected from phosphoric acid, hydrochloric acid and sulfuric acid, and having a pH at 25° C. of 2.5 or more and 6.5 or less.

An aqueous suspension agrochemical composition comprising 1 to 50% by weight of fenpyrazamine, 1 to 50% by weight of procymidone, and 0.01 to 1.0% by weight of one or more acid components selected from phosphoric acid, hydrochloric acid and sulfuric acid, and having a pH at 25° C. of 2.5 or more and 6.5 or less.

An aqueous suspension agrochemical composition comprising 1 to 50% by weight of fenpyrazamine, 1 to 50% by weight of procymidone and 0 to 3.0% by weight of an acid component, and having a pH at 25° C. of 3.0 or more and 6.5 or less.

An aqueous suspension agrochemical composition comprising 1 to 50% by weight of fenpyrazamine, 1 to 50% by weight of procymidone and 0.01 to 2.0% by weight of an acid component, and having a pH at 25° C. of 3.0 or more and 6.5 or less.

An aqueous suspension agrochemical composition comprising 1 to 50% by weight of fenpyrazamine, 1 to 50% by weight of procymidone and 0.01 to 1.0% by weight of an acid component, and having a pH at 25° C. of 3.0 or more and 6.5 or less.

An aqueous suspension agrochemical composition comprising 1 to 50% by weight of fenpyrazamine, 1 to 50% by weight of procymidone, and 0 to 3.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine, 1 to 50% by weight of procymidone, and 0.01 to 2.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine, 1 to 50% by weight of procymidone, and 0.01 to 1.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine, 1 to 50% by weight of procymidone, 0 to 3.0% by weight of an acid component and 0.1 to 10% by weight of a surfactant, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 2.0% by weight of an acid component and 0.1 to 10% by weight of a surfactant, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 1.0% by weight of an acid component and 0.1 to 10% by weight of a surfactant, and having a pH at 25° C. of 2.5 or more and 6.5 or less.

An aqueous suspension agrochemical composition comprising 1 to 50% by weight of fenpyrazamine, 1 to 50% by weight of procymidone, 0 to 3.0% by weight of one or more acid components selected from phosphoric acid, hydrochloric acid and sulfuric acid and 0.1 to 10% by weight of a surfactant, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 2.0% by weight of one or more acid components selected from phosphoric acid, hydrochloric acid and sulfuric acid and 0.1 to 10% by weight of a surfactant, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 1.0% by weight of one or more acid components selected from phosphoric acid, hydrochloric acid and sulfuric acid and 0.1 to 10% by weight of a surfactant, and having a pH at 25° C. of 2.5 or more and 6.5 or less.

An aqueous suspension agrochemical composition comprising 1 to 50% by weight of fenpyrazamine, 1 to 50% by weight of procymidone, 0 to 3.0% by weight of an acid component and 0.1 to 10% by weight of a surfactant, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 2.0% by weight of an acid component and 0.1 to 10% by weight of a surfactant, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 1.0% by weight of an acid component and 0.1 to 10% by weight of a surfactant, and having a pH at 25° C. of 3.0 or more and 6.5 or less.

An aqueous suspension agrochemical composition comprising 1 to 50% by weight of fenpyrazamine, 1 to 50% by weight of procymidone, 0 to 3.0% by weight of one or more acid components selected from phosphoric acid, hydrochloric acid and sulfuric acid and 0.1 to 10% by weight of a surfactant, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 2.0% by weight of one or more acid components selected from phosphoric acid, hydrochloric acid and sulfuric acid and 0.1 to 10% by weight of a surfactant, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 1.0% by weight of one or more acid components selected from phosphoric acid, hydrochloric acid and sulfuric acid and 0.1 to 10% by weight of a surfactant, and having a pH at 25° C. of 3.0 or more and 6.5 or less.

An aqueous suspension agrochemical composition comprising 1 to 50% by weight of fenpyrazamine, 1 to 50% by weight of procymidone, 0 to 3.0% by weight of an acid component and 0.1 to 10% by weight of polyoxyalkylene aryl phenyl ether phosphoric acid ester salt, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 2.0% by weight of an acid component and 0.1 to 10% by weight of polyoxyalkylene aryl phenyl ether phosphoric acid ester salt, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 1.0% by weight of an acid component and 0.1 to 10% by weight of polyoxyalkylene aryl phenyl ether phosphoric acid ester salt, and having a pH at 25° C. of 2.5 or more and 6.5 or less.

An aqueous suspension agrochemical composition comprising 1 to 50% by weight of fenpyrazamine, 1 to 50% by weight of procymidone, 0 to 3.0% by weight of one or more acid components selected from phosphoric acid, hydrochloric acid and sulfuric acid and 0.1 to 10% by weight of polyoxyalkylene aryl phenyl ether phosphoric acid ester salt, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 2.0% by weight of one or more acid components selected from phosphoric acid, hydrochloric acid and sulfuric acid and 0.1 to 10% by weight of polyoxyalkylene aryl phenyl ether phosphoric acid ester salt, and having a pH at 25° C. of 2.5 or more and 6.5 or less.

An aqueous suspension agrochemical composition comprising 1 to 50% by weight of fenpyrazamine, 1 to 50% by weight of procymidone, 0.01 to 1.0% by weight of one or more acid components selected from phosphoric acid, hydrochloric acid and sulfuric acid and 0.1 to 10% by weight of polyoxyalkylene aryl phenyl ether phosphoric acid ester salt, and having a pH at 25° C. of 2.5 or more and 6.5 or less.

An aqueous suspension agrochemical composition comprising 1 to 50% by weight of fenpyrazamine, 1 to 50% by weight of procymidone, 0 to 3.0% by weight of an acid component and 0.1 to 10% by weight of polyoxyalkylene aryl phenyl ether phosphoric acid ester salt, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 2.0% by weight of an acid component and 0.1 to 10% by weight of polyoxyalkylene aryl phenyl ether phosphoric acid ester salt, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 1.0% by weight of an acid component and 0.1 to 10% by weight of polyoxyalkylene aryl phenyl ether phosphoric acid ester salt, and having a pH at 25° C. of 3.0 or more and 6.5 or less.

An aqueous suspension agrochemical composition comprising 1 to 50% by weight of fenpyrazamine, 1 to 50% by weight of procymidone, 0 to 3.0% by weight of one or more acid components selected from phosphoric acid, hydrochloric acid and sulfuric acid and 0.1 to 10% by weight of polyoxyalkylene aryl phenyl ether phosphoric acid ester salt, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 2.0% by weight of one or more acid components selected from phosphoric acid, hydrochloric acid and sulfuric acid and 0.1 to 10% by weight of polyoxyalkylene aryl phenyl ether phosphoric acid ester salt, and having a pH at 25° C. of 3.0 or more and 6.5 or less.

An aqueous suspension agrochemical composition comprising 1 to 50% by weight of fenpyrazamine, 1 to 50% by weight of procymidone, 0.01 to 1.0% by weight of one or more acid components selected from phosphoric acid, hydrochloric acid and sulfuric acid and 0.1 to 10% by weight of polyoxyalkylene aryl phenyl ether phosphoric acid ester salt, and having a pH at 25° C. of 3.0 or more and 6.5 or less.

An aqueous suspension agrochemical composition comprising 1 to 50% by weight of fenpyrazamine, 1 to 10% by weight of sodium lignin sulfonate and 0.01 to 2.0% by weight of one or more acid components selected from phosphoric acid, hydrochloric acid and sulfuric acid, and having a pH at 25° C. of 3.0 or more and 6.5 or less.

An aqueous suspension agrochemical composition comprising 1 to 50% by weight of fenpyrazamine, 1 to 10% by weight of sodium lignin sulfonate and 0.01 to 1.0% by weight of one or more acid components selected from phosphoric acid, hydrochloric acid and sulfuric acid, and having a pH at 25° C. of 3.0 or more and 6.5 or less.

An aqueous suspension agrochemical composition comprising 9 to 40% by weight of fenpyrazamine, 4 to 7% by weight of sodium lignin sulfonate and 0.01 to 2.0% by weight of one or more acid components selected from phosphoric acid, hydrochloric acid and sulfuric acid, and having a pH at 25° C. of 3.0 or more and 6.5 or less.

An aqueous suspension agrochemical composition comprising 9 to 40% by weight of fenpyrazamine, 4 to 7% by weight of sodium lignin sulfonate and 0.01 to 1.0% by weight of one or more acid components selected from phosphoric acid, hydrochloric acid and sulfuric acid, and having a pH at 25° C. of 3.0 or more and 6.5 or less.

An aqueous suspension agrochemical composition comprising 5 to 10% by weight of fenpyrazamine, 20 to 25% by weight of procymidone, and 0.01 to 2.0% by weight of one or more acid components selected from phosphoric acid, hydrochloric acid and sulfuric acid, and having a pH at 25° C. of 3.0 or more and 6.5 or less.

An aqueous suspension agrochemical composition comprising 5 to 10% by weight of fenpyrazamine, 20 to 25% by weight of procymidone, 0.01 to 2.0% by weight of one or more acid components selected from phosphoric acid, hydrochloric acid and sulfuric acid and 0.1 to 5.0% by weight of polyoxyalkylene aryl phenyl ether phosphoric acid ester salt, and having a pH at 25° C. of 3.0 or more and 6.5 or less.

An aqueous suspension agrochemical composition comprising 5 to 10% by weight of fenpyrazamine, 20 to 25% by weight of procymidone, and 0.01 to 1.0% by weight of one or more acid components selected from phosphoric acid, hydrochloric acid and sulfuric acid, and having a pH at 25° C. of 3.0 or more and 6.5 or less.

An aqueous suspension agrochemical composition comprising 5 to 10% by weight of fenpyrazamine, 20 to 25% by weight of procymidone, 0.01 to 1.0% by weight of one or more acid components selected from phosphoric acid, hydrochloric acid and sulfuric acid and 0.1 to 5.0% by weight of polyoxyalkylene aryl phenyl ether phosphoric acid ester salt, and having a pH at 25° C. of 3.0 or more and 6.5 or less.

An aqueous suspension agrochemical composition comprising 5 to 10% by weight of fenpyrazamine, 20 to 25% by weight of procymidone and 0.10 to 1.0% by weight of phosphoric acid, and having a pH at 25° C. of 3.0 or more and 6.5 or less.

An aqueous suspension agrochemical composition comprising 5 to 10% by weight of fenpyrazamine, 20 to 25% by weight of procymidone and 0.10 to 0.7% by weight of phosphoric acid, and having a pH at 25° C. of 3.0 or more and 6.5 or less.

An aqueous suspension agrochemical composition comprising 5 to 10% by weight of fenpyrazamine, 20 to 25% by weight of procymidone, 0.10 to 1.0% by weight of phosphoric acid and 0.1 to 5.0% by weight of polyoxyalkylene aryl phenyl ether phosphoric acid ester salt, and having a pH at 25° C. of 3.0 or more and 6.5 or less.

An aqueous suspension agrochemical composition comprising 5 to 10% by weight of fenpyrazamine, 20 to 25% by weight of procymidone, 0.10 to 0.7% by weight of phosphoric acid and 0.1 to 5.0% by weight of polyoxyalkylene aryl phenyl ether phosphoric acid ester salt, and having a pH at 25° C. of 3.0 or more and 6.5 or less.

The present composition can be produced by mixing fenpyrazamine and water, an acid component, an agrochemical adjuvant and the like. More specifically, water to which a surfactant and the like are added as necessary, and fenpyrazamine are mixed, and fenpyrazamine is finely pulverized using a wet pulverizer such as a bead mill to prepare a fenpyrazamine suspension. Alternatively, it is also possible that fenpyrazamine is finely pulverized using a dry pulverizer such as a jet mill, and then water to which a surfactant and the like are added as necessary and the pulverized fenpyrazamine are mixed to prepare a fenpyrazamine suspension. Moreover, a thickener and the like are added to the fenpyrazamine suspension as necessary, and the pH at 25° C. is measured by the above method, and an acid component is added such that the pH may be in the range of 3 to 7, whereby the present composition can be obtained. Here, the timing of the acid component addition does not matter.

In the present composition, fenpyrazamine is dispersed in water in the form of fine particles. The average particle diameter of the fine particles is usually 10 μm or less, and preferably 0.2 to 5 μm.

In the present invention, the average particle diameter means a volume median diameter. The volume median diameter refers to a particle diameter at which a cumulative frequency in a volume-based frequency distribution is to be 50%, and can be obtained, for example, by wet measurement using a laser diffraction particle size distribution measuring apparatus. More specifically, the present composition is added dropwise to water and dispersed, and the volume median diameter is measured using the apparatus. Examples of the laser diffraction particle size distribution measuring apparatus include Mastersizer 2000 (manufactured by Malvern Instruments Ltd).

The present composition can be applied to places such as paddy fields, cultivated lands, orchards, grass plot, and non-agricultural lands, in the same manner as in the case of the normal aqueous suspension agrochemical composition. The present composition is diluted with water as desired, and can be applied by a method in which the obtained water dilution is sprayed on plants growing in the above places or the soil in the above places, or the like. The method for spraying the water dilution includes a soil surface application or foliage application of the water dilution using a known sprinkler or the like, and the like.

It is also possible to use the water dilution in a seed treatment, a seedling raising box treatment, and the like.

The present composition can be also applied as it is without being diluted with water and, a method for spraying the present composition along from levee to levee of paddy fields under flooding and the like is exemplified. Before spraying, the present composition is usually mixed by slightly shaking a vessel containing the present composition.

EXAMPLES

The present invention will be described in further detail below by way of Examples.

First, production examples and comparative production examples will be shown. Here, % described in production examples and comparative production examples is mass percent concentration.

Production Example 1

40 Parts by weight of fenpyrazamine, 7 parts by weight of sodium lignin sulfonate (trade name: Reax 85A, manufactured by MeadWestvaco Corporation, weight average molecular weight of 10000, sulfonation degree of 0.8), 5 parts by weight of propylene glycol, 0.2 parts by weight of a silicone-based antifoaming agent (trade name: Antifoam C emulsion, manufactured by Dow Corning Toray Co., Ltd.), 1.0 parts by weight of a mixture of silicone oxide and aluminum oxide (trade name: Aerosil COK-84, manufactured by NIPPON AEROSIL CO., LTD.) and 26.8 parts by weight of ion exchange water were mixed, and then wet-pulverized using DYNO-MILL KDL (manufactured by SHINMARU ENTERPRISES CORPORATION) to obtain a suspension. On the other hand, 0.15 parts by weight of xanthan gum (trade name: Kelzan S, manufactured by CP Kelco) and 0.2 parts by weight of a preservative (trade name: Proxel GXL, manufactured by Lonza Group Ltd.) were added to 19.65 parts by weight of ion exchange water, and the mixture was continuously stirred for 1 hour to obtain a thickener solution. The thickener solution was added to the suspension and mixed, and then 0.32 parts by weight of phosphoric acid (85% aqueous solution) was added thereto so that the mixed liquid had a pH of 6.0, to obtain the aqueous suspension agrochemical composition of the present invention (hereinafter referred to as Present Composition (1)).

Production Example 2

The same procedure was carried out as in Production Example 1, except that the thickener solution was added to the suspension and mixed, and then 0.47 parts by weight of phosphoric acid (85% aqueous solution) was added thereto so that the mixed liquid had a pH of 5.0, to obtain the aqueous suspension agrochemical composition of the present invention (hereinafter referred to as Present Composition (2)).

Production Example 3

The same procedure was carried out as in Production Example 1, except that the thickener solution was added to the suspension and mixed, and then 0.76 parts by weight of phosphoric acid (85% aqueous solution) was added thereto so that the mixed liquid had a pH of 4.0, to obtain the aqueous suspension agrochemical composition of the present invention (hereinafter referred to as Present Composition (3)).

Production Example 4

The same procedure was carried out as in Production Example 1, except that the thickener solution was added to the suspension and mixed, and then 1.16 parts by weight of phosphoric acid (85% aqueous solution) was added thereto so that the mixed liquid had a pH of 3.0, to obtain the aqueous suspension agrochemical composition of the present invention (hereinafter referred to as Present Composition (4)).

Production Example 5

The same procedure was carried out as in Production Example 1, except that the thickener solution was added to the suspension and mixed, and then 0.3 parts by weight of hydrochloric acid (36% aqueous solution) was added thereto so that the mixed liquid had a pH of 6.0, to obtain the aqueous suspension agrochemical composition of the present invention (hereinafter referred to as Present Composition (5)).

Production Example 6

The same procedure was carried out as in Production Example 1, except that the thickener solution was added to the suspension and mixed, and then 0.16 parts by weight of sulfuric acid (96% aqueous solution) was added thereto so that the mixed liquid had a pH of 6.0, to obtain the aqueous suspension agrochemical composition of the present invention (hereinafter referred to as Present Composition (6)).

Production Example 7

10 Parts by weight of fenpyrazamine, 25 parts by weight of procymidone, 4 parts by weight of sodium lignin sulfonate (trade name: Reax 85A, manufactured by MeadWestvaco Corporation, weight average molecular weight of 10000, sulfonation degree of 0.8), 1 part by weight of polyoxyethylene tristyrylphenyl ether phosphate triethanolamine salt (trade name: SOPROPHOR FL, manufactured by Rhodia), 5 parts by weight of propylene glycol, 0.2 parts by weight of a silicone-based antifoaming agent (trade name: Antifoam A compound, manufactured by Dow Corning Toray Co., Ltd.) and 43.1 parts by weight of ion exchange water were mixed, and then wet-pulverized using DYNO-MILL KDL (manufactured by SHINMARU ENTERPRISES CORPORATION) to obtain a suspension. On the other hand, 0.2 parts by weight of xanthan gum (trade name: Kelzan S, manufactured by CP Kelco), 0.4 parts by weight of aluminum magnesium silicate (trade name: Veegum R, manufactured by R.T. Vanderbilt Company, Inc.) and 0.2 parts by weight of a preservative (trade name: Proxel GXL, manufactured by Lonza Group Ltd.) were added to 25.9 parts by weight of ion exchange water, and the mixture was continuously stirred for 1 hour to obtain a thickener solution. The thickener solution was added to the suspension and mixed, and then 0.29 parts by weight of phosphoric acid (85% aqueous solution) was added thereto so that the mixed liquid had a pH of 6.0, to obtain the aqueous suspension agrochemical composition of the present invention (hereinafter referred to as Present Composition (7)).

Production Example 8

The same procedure was carried out as in Production Example 7, except that the thickener solution was added to the suspension and mixed, and then 0.43 parts by weight of phosphoric acid (85% aqueous solution) was added thereto so that the mixed liquid had a pH of 5.0, to obtain the aqueous suspension agrochemical composition of the present invention (hereinafter referred to as Present Composition (8)).

Production Example 9

The same procedure was carried out as in Production Example 7, except that the thickener solution was added to the suspension and mixed, and then 0.53 parts by weight of phosphoric acid (85% aqueous solution) was added thereto so that the mixed liquid had a pH of 4.0, to obtain the aqueous suspension agrochemical composition of the present invention (hereinafter referred to as Present Composition (9)).

Production Example 10

The same procedure was carried out as in Production Example 7, except that the thickener solution was added to the suspension and mixed, and then 0.76 parts by weight of phosphoric acid (85% aqueous solution) was added thereto so that the mixed liquid had a pH of 3.0, to obtain the aqueous suspension agrochemical composition of the present invention (hereinafter referred to as Present Composition (10)).

Production Example 11

The same procedure was carried out as in Production Example 7, except that the thickener solution was added to the suspension and mixed, and then 0.26 parts by weight of hydrochloric acid (36% aqueous solution) was added thereto so that the mixed liquid had a pH of 6.0, to obtain the aqueous suspension agrochemical composition of the present invention (hereinafter referred to as Present Composition (11)).

Production Example 12

The same procedure was carried out as in Production Example 7, except that the thickener solution was added to the suspension and mixed, and then 0.13 parts by weight of sulfuric acid (96% aqueous solution) was added thereto so that the mixed liquid had a pH of 6.0, to obtain the aqueous suspension agrochemical composition of the present invention (hereinafter referred to as Present Composition (12)).

Production Example 13

10 Parts by weight of fenpyrazamine, 25 parts by weight of procymidone, 4 parts by weight of sodium lignin sulfonate (trade name: Reax 85A, manufactured by MeadWestvaco Corporation, weight average molecular weight of 10000, sulfonation degree of 0.8), 2.5 parts by weight of polyoxyethylene tristyrylphenyl ether phosphate potassium salt (trade name: SOPROPHOR FLK, manufactured by Rhodia), 3.5 parts by weight of propylene glycol, 0.2 parts by weight of a silicone-based antifoaming agent (trade name: Antifoam A compound, manufactured by Dow Corning Toray Co., Ltd.) and 43.1 parts by weight of ion exchange water were mixed, and then wet-pulverized using DYNO-MILL KDL (manufactured by SHINMARU ENTERPRISES CORPORATION) to obtain a suspension. On the other hand, 0.2 parts by weight of xanthan gum (trade name: Kelzan S, manufactured by CP Kelco), 0.4 parts by weight of aluminum magnesium silicate (trade name: Veegum R, manufactured by R.T. Vanderbilt Company, Inc.)

and 0.2 parts by weight of a preservative (trade name: Proxel GXL, manufactured by Lonza Group Ltd.) were added to 25.9 parts by weight of ion exchange water, and the mixture was continuously stirred for 1 hour to obtain a thickener solution. The thickener solution was added to the suspension and mixed, and then 0.28 parts by weight of phosphoric acid (85% aqueous solution) was added thereto so that the mixed liquid had a pH of 6.5, to obtain the aqueous suspension agrochemical composition of the present invention (hereinafter referred to as Present Composition (13)).

Comparative Production Example 1

The same procedure was carried out as in Production Example 1, except that the thickener solution was added to the suspension and mixed, and then 0.08 parts by weight of phosphoric acid (85% aqueous solution) was added thereto so that the mixed liquid had a pH of 7.5, to obtain the aqueous suspension agrochemical composition for comparison (hereinafter referred to as Comparative Composition (1)).

Comparative Production Example 2

The same procedure was carried out as in Production Example 1, except that the thickener solution was added to the suspension and mixed, and then 1.9 parts by weight of phosphoric acid (85% aqueous solution) was added thereto so that the mixed liquid had a pH of 2.0, to obtain the aqueous suspension agrochemical composition for comparison (hereinafter referred to as Comparative Composition (2)).

Comparative Production Example 3

The same procedure was carried out as in Production Example 7, except that the thickener solution was added to the suspension and mixed, and then 0.1 parts by weight of phosphoric acid (85% aqueous solution) was added thereto so that the mixed liquid had a pH of 7.5, to obtain the aqueous suspension agrochemical composition for comparison (hereinafter referred to as Comparative Composition (3)).

Comparative Production Example 4

The same procedure was carried out as in Production Example 7, except that the thickener solution was added to the suspension and mixed, and then 1.37 parts by weight of phosphoric acid (85% aqueous solution) was added thereto so that the mixed liquid had a pH of 2.0, to obtain the aqueous suspension agrochemical composition for comparison (hereinafter referred to as Comparative Composition (4)).

Next, a test example will be shown.

Test Example 1

Each 50 mL of Present Compositions (1) to (13) and Comparative Compositions (1) to (4) was put in a glass bottle and sealed, and allowed to stand still in a thermostat at 54° C. for 2 weeks. Thereafter, odor sensory test of each aqueous suspension agrochemical composition was performed. The odor sensory test was performed by three panelists, and determination was made through discussion. The determination criteria are as described below.

Determination Criteria

−: There is no odor derived from fenpyrazamine
+: There is slight odor derived from fenpyrazamine
++: There is strong odor derived from fenpyrazamine The result is shown in Table 1. Here, Comparative Composition (2) was solidified during 2 weeks of storage at 54° C., thus could not maintain the suspension state. Also, Comparative Composition (4) generated aggregates during 2 weeks of storage at 54° C., thus could not maintain the suspension state.

TABLE 1

| Aqueous suspension agrochemical composition | Acid component | pH | Odor after 2 weeks storage at 54° C. |
|---|---|---|---|
| Present Composition (1) | Phosphoric acid | 6.0 | + ~ − |
| Present Composition (2) | | 5.0 | − |
| Present Composition (3) | | 4.0 | − |
| Present Composition (4) | | 3.0 | − |
| Present Composition (5) | Hydrochloric acid | 6.0 | + ~ − |
| Present Composition (6) | Sulfuric acid | 6.0 | + ~ − |
| Present Composition (7) | Phosphoric acid | 6.0 | − |
| Present Composition (8) | | 5.0 | − |
| Present Composition (9) | | 4.0 | − |
| Present Composition (10) | | 3.0 | − |
| Present Composition (11) | Hydrochloric acid | 6.0 | − |
| Present Composition (12) | Sulfuric acid | 6.0 | + ~ − |
| Present Composition (13) | Phosphoric acid | 6.5 | + ~ − |
| Comparative Composition (1) | Phosphoric acid | 7.5 | ++ ~ + |
| Comparative Composition (3) | Phosphoric acid | 7.5 | ++ ~ + |

The invention claimed is:

1. A method of making an aqueous suspension agrochemical composition comprising fenpyrazamine, the method comprising:
    a) suspending 1 to 50% by weight of fenpyrazamine in 30 to 80% by weight of water, based on 100% by weight of the composition, and
    b) adding an acid component
    such that the composition has a pH at 25° C. in a range of 2.5 to 6.5, and wherein the composition has no problem of odor emission.

2. The method of claim 1, wherein the acid component is at least one selected from the group consisting of phosphoric acid, hydrochloric acid, and sulfuric acid.

3. The method of claim 2, further comprising adding procymidone.

4. The method of claim 2, further comprising adding polyoxyalkylene aryl phenyl ether phosphoric acid ester salt.

5. The method of claim 1, further comprising adding procymidone.

6. The method of claim 5, further comprising adding polyoxyalkylene aryl phenyl ether phosphoric acid ester salt.

7. The method of claim 1, wherein the fenpyrazamine is pulverized using a wet pulverizer.

8. The method of claim 1, wherein the fenpyrazamine is dispersed in the water in the form of fine particles having an average diameter of 10 μm or less.

9. The method of claim 1, wherein the acid component is added to the aqueous suspension.

* * * * *